United States Patent [19]

Sandquist

[11] Patent Number: 4,519,106
[45] Date of Patent: May 28, 1985

[54] SPINE BOARD

[76] Inventor: Ralph Sandquist, R.D. #3, Jamestown, N.Y. 14701

[21] Appl. No.: 255,269

[22] Filed: Aug. 19, 1981

[51] Int. Cl.³ ............................................. A61G 7/08
[52] U.S. Cl. ...................................... 5/82 R; 128/134
[58] Field of Search ...................... 5/81 R, 82 R, 82 B, 5/431, 494; 128/134, 133, 135; 2/312-322, 338; 224/252, 269

[56] References Cited

U.S. PATENT DOCUMENTS

| 899,828 | 9/1908 | Czarnkowsky | 2/314 |
| 1,074,498 | 9/1913 | Eiker | 2/316 |
| 1,525,464 | 2/1925 | Parke | 2/315 |
| 2,366,082 | 12/1944 | Baker | 5/82 R |
| 2,607,050 | 8/1952 | Binschoff | 5/81 R |
| 2,705,328 | 4/1955 | Felix | 2/312 |
| 3,057,354 | 10/1962 | Roberts et al. | 2/319 |
| 4,127,120 | 11/1978 | Applegate | 5/82 R |
| 4,172,453 | 10/1979 | Leckie | 128/133 |
| 4,226,231 | 10/1980 | Anderson | 128/134 |

FOREIGN PATENT DOCUMENTS

| 1349543 | of 1974 | United Kingdom | 5/82 R |
| 563976 | of 1977 | U.S.S.R. | 5/82 R |

Primary Examiner—Alexander Grosz
Assistant Examiner—Michael F. Trettel

[57] ABSTRACT

A spine board having openings for receiving the clasps of a strap member that is adapted to secure the torso of an accident victim to the board for immobility, the strap member carrying a plurality of slidably disposed clasps that secure to predetermined locations on the board with the strap having free ends with buckle and catch members that engage to secure the torso to the spine board.

3 Claims, 6 Drawing Figures

SPINE BOARD

BACKGROUND OF THE INVENTION

This invention relates to spine boards against which the torso of an accident victim is secured to be immobile while being transported for treatment. The victim is attached to the board in a conventional manner by straps of the automobile safety strap type. The straps carry hooks that are fixed to pins on the board with the strap passing around the torso to fasten the victim to the board. The attendant can then handle and position the victim by grasping the board and transporting the victim without the torso and spine area moving causing further damage to the victim.

In the past the strap member carried hooks or clasps that were fixed in position on the strap requiring the strap to be passed about the torso in a specific complicated fashion.

SUMMARY OF THE INVENTION

It is an object of this invention to provide a spine board with a torso securing strap that attaches to the board in a manner permitting the strap to cross over the upper portion of the torso, cross over the lower portion of the torso and crisscross over the torso to securely fasten the torso to the board.

It is a further object of this invention to provide a strap for a spine board having sliding hooks or clasp members permitting easy installation of the strap on the board.

It is another object of this invention to provide handles for a spine board that attach to the back surface of the board and extend into the securing opening of the board and flush with the board front surface to be easily accessible and securely fastened to the board.

FIGURES OF THE DRAWING

Figure 1:
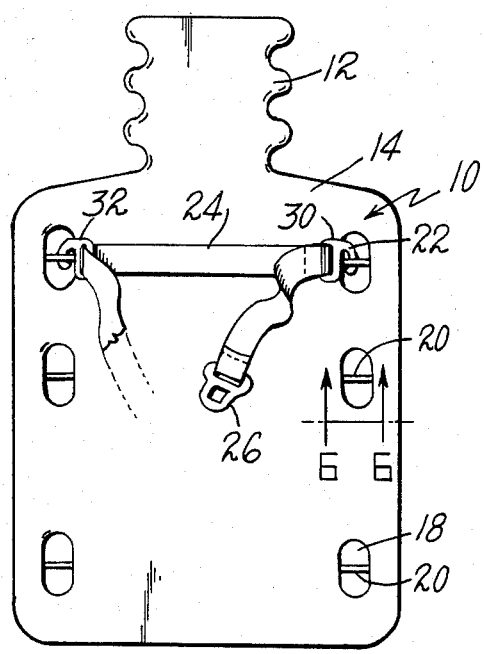
FIG. 1 illustrates the spine board with the hooks and strap in the first and second positions of attachment.
Figure 2:
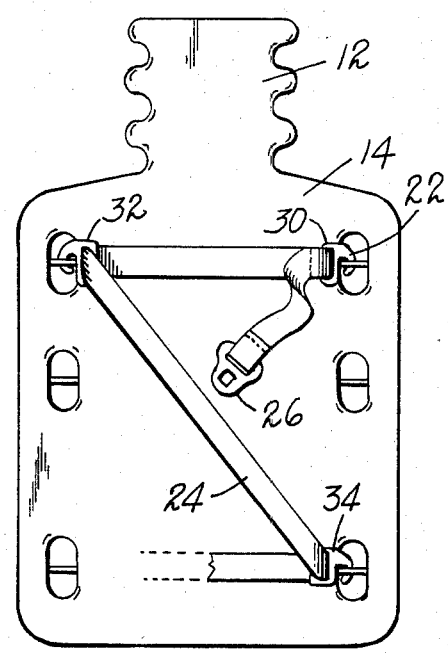
FIG. 2 illustrates the spine board with the hooks and strap in third position of attachment.
Figure 3:
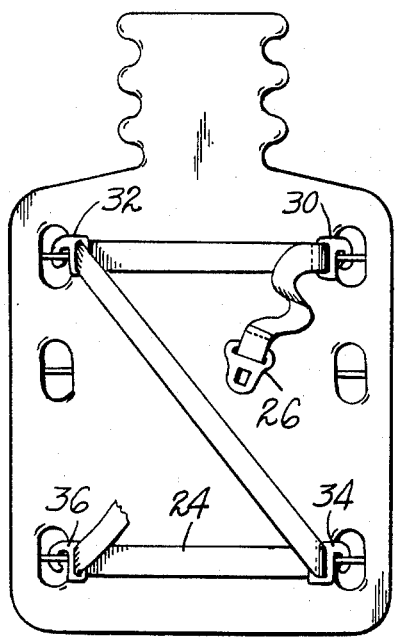
FIG. 3 illustrates the spine board with the hooks and strap in the fourth position of attachment.
Figure 4:
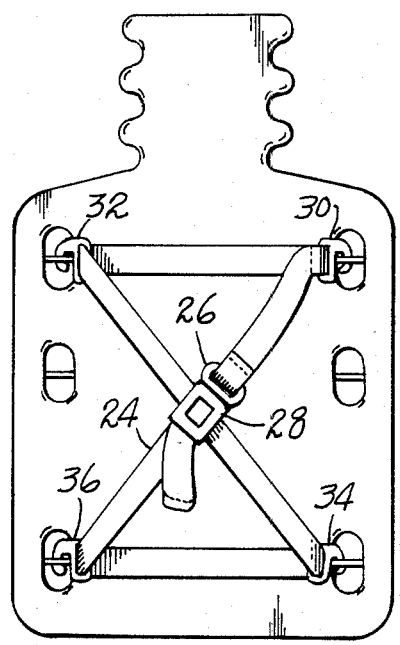
FIG. 4 illustrates the spine board with the hooks and strap installed and the buckle and catch on the free ends of the strap being secured.

Attention is now directed to the drawing which illustrates a spine board (10) of conventional configuration. The spine board has a head support area (12), shoulder support area (14) and torso support area (16). The torso support area has openings (18) into which handles (20) project.

The handles (20) are adapted to receive the hooks (22) carried on the attaching strap (24) which passes around the torso area of the patient to secure the patient to the spine board.

The free ends of the strap have a catch (26) and buckle (28) of the releasable type. The hooks (22), strap (24), catch (26) and buckle (28) are all the automobile safety belt type construction.

The hook (30), catch (26) and buckle (28) are all fixed in position on the strap (24) by overlap stitching as illustrated. The remaining hooks (32)–(36) are all slidably carried on the strap (24) by the strap (24) passing through the opening (38) in each of the hooks.

With the hook and strap combination thus described, the patient can be secured to the spine board in the following manner: after the board is slid under the back of the patient, the hook (30) is secured to any one of the handles (20). The strap then passes over the patients torso to the opposite handle (20) to which hook (32) is attached. The strap is then passed over the torso to the diagonally disposed handle (20) to which the hook (34) is attached. The strap then is positioned over the torso to the opposite handle (20) to which hook (36) is attached. Thereafter, the catch (26) and buckle (28) are brought together and the entire strap assembly tightened in the manner of an automobile seat belt to secure the torso of the patient to the spine board.

The hook and strap combination of this invention greatly facilitates securing the patient to the board. It can be seen that the strap can be secured regardless to which handle the hook (30) is first attached. As long as the opposite, diagonally opposite and opposite handles are used the torso can be secured to the board in upper and lower torso area and secured in crisscross fashion across the chest area.

Figure 5:
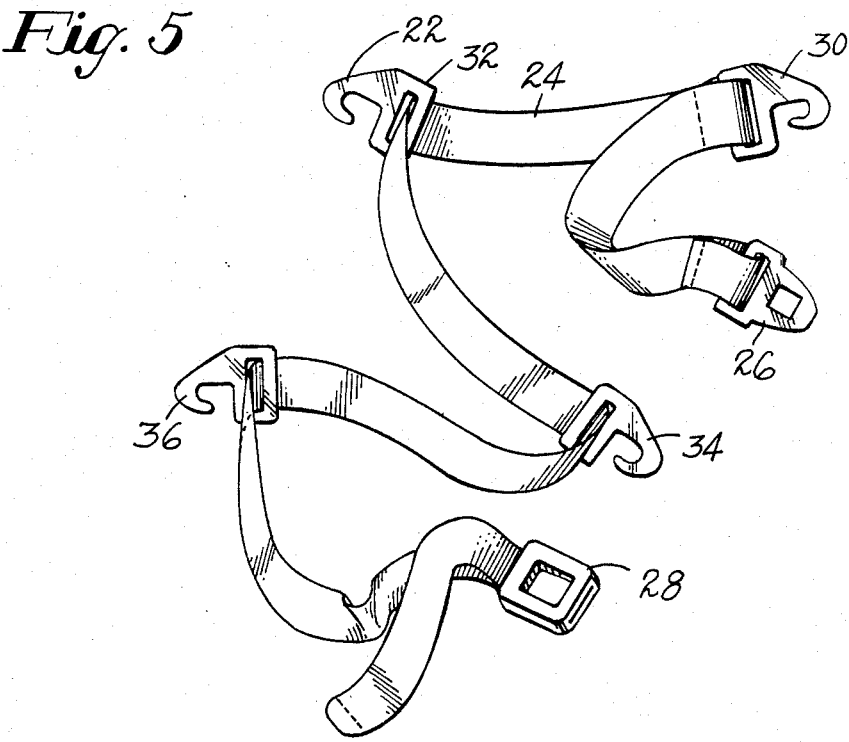
FIG. 5 illustrates the hooks and straps in their free position.

Attention is now directed to FIG. 5 which illustrates the hooks and strap in their free state disassembled from the board. It should be noted in this figure that the hook (34) is disposed opposite the hooks (30), (32) and (36) to insure that the strap will not twist but will lay flat on the torso when installed on the board.

Figure 6:
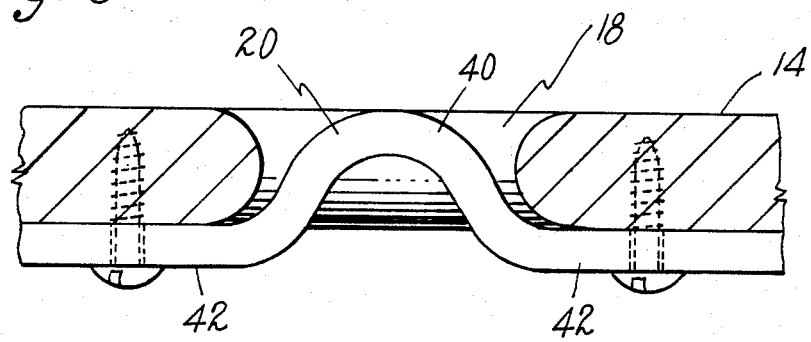
FIG. 6 is an enlarged sectional view of the handles to which the hooks attach, taken along the Line 6—6 of FIG. 1.

FIG. 6 illustrates the handles (20) and their attachment means to the board. The handles (20) have a securing portion (40) and leg portions (42) which are riveted or otherwise secured to the back of the board. The securing portion (40) of handles (20) is raised and passes into opening (18) to be flush with the front of the board and accessible to the hooks on the securing strap.

With the invention thus described, it can be seen that a unique strap and hook combination has been provided that is easily adapted and installed on a conventional spine board.

I claim:

1. A spine board having openings with attachment means for receipt of hooks carried on a securing strap adapted to pass around a patient's torso to secure the torso to the board; comprising:
   (a) a board having a substantially rectangular configuration with openings adjacent the opposite edges of the board;
   (b) securing means comprising handles in the board openings;
   (c) a hook and strap combination;
   (d) said strap having a buckle on one free end and a catch on the other free end;
   (e) a plurality of hooks carried on strap and freely slidable thereon;
   (f) said hooks adapted to engage said handles with the strap passing about a patient's torso and with the buckle and catch locked, the strap being freely tightened to secure the torso to the board; and
   (g) at least one of said hooks is permanently fixed to said strap with at least three remaining hooks being feely slidable on the strap.

2. The spine board of claim 1 wherein an intermediate hook is placed on the strap opposite the remaining hooks to insure that the strap lays flat on the patient's torso.

3. In combination, a spine board and a hook and strap combination adapted to secure a patient's torso to said spine board and comprising:
 (a) a strap member having free ends with a buckle secured to one free end and a catch secured to the other;
 (b) a plurality of hooks carried on said strap member;
 (c) at least one of said hooks being fixed in position on said strap member with the remaining hooks being freely slidable on said strap.

* * * * *